United States Patent [19]

Scott et al.

[11] Patent Number: 5,243,107

[45] Date of Patent: Sep. 7, 1993

[54] CHEMICAL PROCESS

[75] Inventors: John D. Scott, Nr Northwich; Rachel A. Steven, Manley, both of England

[73] Assignee: Imperial Chemical Industries PLC, London, England

[21] Appl. No.: 755,551

[22] Filed: Sep. 5, 1991

Related U.S. Application Data

[63] Continuation-in-part of Ser. No. 676,703, Mar. 29, 1991, abandoned.

[30] Foreign Application Priority Data

Mar. 29, 1990 [GB] United Kingdom ............... 9007029

[51] Int. Cl.$^5$ ..................... C07C 17/08; C07C 17/00
[52] U.S. Cl. .................................. 570/166; 570/165; 570/167; 570/168; 570/169
[58] Field of Search ............... 570/165, 166, 167, 168, 570/169

[56] References Cited

U.S. PATENT DOCUMENTS 2,005,710  6/1935  Davdt ............................... 570/167
4,605,798  8/1986  Abel ................................ 570/167

Primary Examiner—Alan Siegel
Attorney, Agent, or Firm—Cushman, Darby & Cushman

[57] ABSTRACT 1,1,1,2-tetrafluoroethane (HFA 134a) is manufactured from trichloroethylene by a two-stage process comprising reacting trichloroethylene with hydrogen fluoride in one reactor to form 1,1,1-trifluoro-2-chloroethane (133a) and reacting the 1,1,1-trifluoro-2-chloroethane with hydrogen fluoride in another reactor to form 1,1,1,2-tetrafluoroethane. The invention is characterised by reversing the reactor sequence and passing the entire product stream from the HFA 134a reactor together with trichloroethylene through the 133a reactor and separating 134a and hydrogen chloride from the recycle stream between the 133a reactor and the 134a reactor.

10 Claims, No Drawings

CHEMICAL PROCESS

This application is a continuation-in-part of Ser. No. 07/676,703, filed Mar. 29, 1991 now abandoned.

This invention relates to a chemical process and more particularly to a process for the manufacture of 1,1,1,2-tetrafluoroethane, known generally as HFA 134a.

Several methods have been proposed for the manufacture of 1,1,1,2-tetrafluoroethane (HFA 134a) which is useful as a replacement for CFCs in refrigeration and other applications. In United Kingdom Patent Specification No. 1,589,924 there is described the production of HFA 134a by the vapour phase fluorination of 1,1,1-trifluoro-2-chloroethane (HCFC 133a) which is itself obtainable by the fluorination of trichloroethylene as described in United Kingdom Patent Specification No. 1,307,224. Unfortunately, the yield of HFA 134a obtained in practice is significantly less than the calculated equilibrium yield. The formation of HFA 134a as a minor product of the fluorination of trichloroethylene is described in United Kingdom Patent Specification No. 819,849, the major reaction product being HCFC 133a.

It has now been found that a modified reaction sequence as hereinafter described, provides significantly improved yields of the desired product.

Thus according to the invention, there is provided a method for the manufacture of 1,1,1,2-tetrafluoroethane which comprises the steps of:

(A) contacting a mixture of 1,1,1,-trifluoro-2-chloroethane and hydrogen fluoride with a fluorination catalyst at a temperature in the range of about 280° to 450° C. in a first reaction zone to form a product containing 1,1,1,2-tetrafluoroethane and hydrogen chloride together with unreacted starting materials, (B) passing the total product of step A together with trichloroethylene to a second reaction zone containing a fluorination catalyst at a temperature in the range of about 200°-400° C. but lower than the temperature in step A to form a product containing 1,1,1,-trifluoro-2-chloroethane, 1,1,1,2-tetrafluoroethane, hydrogen chloride and trichloroethylene, (C) treating the product of step B to separate 1,1,1,2-tetrafluoroethane and hydrogen chloride from 1,1,1-trifluoro-2-chloroethane, unreacted hydrogen fluoride and trichloroethylene, (D) feeding the 1,1,1-trifluoro-2-chloroethane mixture obtained from step C together with hydrogen fluoride to said first reaction zone (step A), and (E) recovering 1,1,1,2-tetrafluoroethane from the 1,1,1,2-tetrafluoroethane and hydrogen chloride separated out in step C.

The fluorination catalyst employed in steps A and B of the method of the invention may be supported or unsupported. Any of the fluorination catalysts described in the prior art may be used including various inorganic compounds, for example oxides, halides and oxyhalides of metals such as aluminium, cobalt, manganese, iron and especially chromium. Suitable chromium-containing catalysts include the oxide, hydroxide, oxyhalide, halides, inorganic acid salts, basic chromium fluoride and the catalysts described in United Kingdom Patent Specification No. 1,307,224. Preferred catalysts are chromia and a zinc or nickel promoted chromia. Such catalysts may be given a prefluorination treatment by passing hydrogen fluoride with or without nitrogen diluent over the catalyst at about 250°–450° C. to condition the catalyst prior to use.

The catalysts may be compressed into pellets and used in a fixed bed or, alternatively, catalysts of appropriate particle size may be used in a moving bed such as a fluidised bed.

A wide range of amounts of hydrogen fluoride may be employed in step A of the method of the invention, ranging from well below the stoichiometric amount to well above this amount. Typical amounts include from 1 to 10 moles, and preferably from 2 to 6 moles, of hydrogen fluoride per mole of 1,1,1-trifluoro-2-chloroethane. Accordingly, the product of this reaction step will usually contain unreacted hydrogen fluoride in addition to 1,1,1,2-tetrafluoroethane, hydrogen chloride and by-products. Preferred reaction temperatures for this stage of the process are in the range from 285°0 to 385° C., especially 300° to 385° C. and more especially 325° to 385° C., with contact times of from 1 to 100 and preferably from 5 to 30 seconds at a pressure of 5 to 20 bars.

From 10 to 100, preferably from 15 to 60, moles of hydrogen fluoride per mole of trichloroethylene are typically employed in Step B. Again, the reaction product of this stage will normally contain unreacted hydrogen fluoride and perhaps low levels of unreacted trichloroethylene. Contact times of up to 100 seconds, preferably 5 to 30 seconds may be used, typically at 220°-350° C. and 5 to 20 bars pressure.

Step A and step B of the process and usually at least step C will usually be carried out under the same pressure which may be, for example, 1 to 30 bars.

The operating pressure for the method of the invention is thus usually dependent on the product work-up scheme employed but is generally within the range from 1 to 30 bars.

The reaction and separation steps which make up the method of the invention may be performed using conventional equipment and techniques. Thus, for example, recovery of 1,1,1,2-tetrafluoroethane in step E may be effected by washing the gaseous tetrafluoroethane with water and aqueous sodium hydroxide solution and then drying and condensing the tetrafluoroethane.

It is preferred that the method of the invention is operated continuously. In practice, however, catalyst deactivation usually occurs requiring discontinuous operation of the process to permit catalyst regeneration or reactivation which may be conveniently effected by passing air or a mixture of air and inert gas, for example nitrogen, over the catalyst at a temperature in the range of 300° to 500° C. A preferred catalyst reactivation process comprises heating the catalyst in a mixture of air and hydrogen fluoride, the resulting hot hydrogen fluoride being useable directly in step A (or step B) of the method according to the invention. The frequency of catalyst regeneration may be reduced if air is added to the reaction mixture in step A and step B of the process.

A particularly useful feature of the invention is that the exothermic conversion of trichloroethylene to 1,1,1-trifluoro-2-chloroethane in step B may be performed in a low cost adiabatic reactor, thereby providing significant cost advantages over reactor systems employing internal cooling surfaces. If desired, step A may also be carried out in an adiabatic reactor.

As stated hereinbefore, the temperature employed in step B of the process is lower than the temperature employed in step A of the process. The recycle stream from step A may require cooling to or to below the temperature used in step B and a useful technique comprises mixing the trichloroethylene feed to step B with the recycle stream in advance of the step B reactor; in this way the recycle stream is cooled by the trichloroethylene whilst at the same time the trichloroethylene is heated, thereby reducing the need for external heating.

Separation of 1,1,1,2-tetrafluoroethane and hydrogen chloride from the product stream in step C of the process may be effected by a distillation technique. The separation of hydrogen chloride from the product stream is desirable since the presence of hydrogen chloride in the recycle stream (step D) would reduce the degree of conversion of 1,1,1-trifluoro-2-chloroethane to 1,1,1,2-tetrafluoroethane achieved in step A; for this reason it is preferred to remove the hydrogen chloride as completely as is reasonably practicable.

The process of the invention is advantageous in that the HFA 134a collected from step B of the process may contain only a small amount, for example 10 to 40 ppm, of the toxic impurity 1-chloro-2,2-difluoroethylene, commonly known as 1122 compared with the amount, for example 200 to 1000 ppm, contained in HFA 134a produced in step A of the process. The procedure employed in the work-up of the product stream from step B (including the separation of step C) will usually contain one or more provisions for removing the 1122 which owing to its similar boiling point to HFA 134a tends to stay with the HFA 134a during the work-up operations.

At least part of the 1122 can be removed from the product stream prior to separation step C by contacting the product stream from step B together with hydrogen fluoride (already present in the product stream) over a fluorination catalyst such as chromia at a temperature in the range of 150° to 250° C. Any 1122 present in the HFA 134a after step C can be removed by azeotropic distillation or extractive distillation and/or by contacting the HFA 134a with a zeolite molecular sieve.

The invention is illustrated but not limited by the following Example.

EXAMPLE 1

For the purpose of comparison with the method of the invention 1,1,1,2-tetrafluoroethane was produced in a two-reactor system comprising a first reactor for converting trichloroethylene to 1,1,1-trifluoro-2-chloroethane and a second reactor for converting the 1,1,1-trifluoro-2-chloroethane to 1,1,1,2-tetrafluoroethane (ie the reverse of the reactor sequence according to the present invention). The trichloroethylene and hydrogen fluoride were fed to the first, low temperature reactor (273° C.) at 13.5 bar. g. to convert the trichloroethylene selectively to 1,1,1-trifluoro-2-chloroethane (133a). The products of reactor 1 were then passed to a second, higher temperature, reactor operating at 366° C. and 13.5 bar. g. where the 133a produced in stage 1 was partially converted to HFA 134a. 133a was included in the feed to the 1st reactor together with the hydrogen fluoride and trichloroethylene to simulate a typical feed including recycle of 133a, HF and a small amount of trichloroethylene from the second reactor. Using an HF:Organics molar ratio of 3.5:1 at the first stage, and a 15% molar trichloroethylene content in the organics feed 133a to give a contact time of 13.5 seconds in each reactor, the reaction efficiencies for the two reactor system were measured and these are presented in Table 1.

To demonstrate the invention, the above order of the series reactors was reversed. In this scheme, the same trichloroethylene and HF feed rates were employed with the same 133a and HF additions to simulate a recycle feed (as above),recycle rates, but the trichloroethylene was introduced into the reactor scheme between the two reactors. The reactor temperatures were also reversed so that the first reactor was operated at the higher reaction temperature (366° C.) for HFA 134a production. Results shown in Table 1.

The process according to the invention was found to give significant reaction conversion advantages to HFA 134a as well as an increase in reaction selectivity. In addition, the process according to the invention also has the advantage of significantly decreasing the level of the toxic unsaturated impurity 1-chloro-2,2-difluoroethylene in the HFA 134a product from 933 ppm in the comparative process to 16 ppm in the method of the invention.

TABLE 1

| Reactor No. 1 | Reactor No. 2 | Trichloroethylene Conversion (%) | % Yields from trichloroethylene | | | R134a Selectivity (%) | R134a + R133a Selectivity (%) | CHCl:CF$_2$ Level in organic product (ppm) |
|---|---|---|---|---|---|---|---|---|
| | | | R133a | R134a | By-Products | | | |
| Comparison (Series) Reactors | | | | | | | | |
| 273° | 366° C. | 99.5 | 16.7 | 76.3 | 6.5 | 76.6 | 91.4 | 933 |
| Invention (Reverse Series Reactors) | | | | | | | | |
| 366° C. | 275° C. | 97.8 | 0.0 | 93.7 | 4.1 | 95.8 | 95.8 | 16 |

EXAMPLE 2

For purposes of comparison a reactor was charged with chromia catalyst and used to react trichloroethylene with hydrogen fluoride at 250° C. and atmospheric pressure with a contact time of 10 seconds. The conversion and selectivities observed are shown in Table 2.

For further purposes of comparison a second reactor was charged with chromia catalyst and the product stream from the first reactor (above) was passed through the second reactor at a temperature of 360° C. and atmospheric pressure with a contact time of 1 second. Using an HF:Organics molar ratio of 3:5:1 and a 15% molar trichloroethylene content in the organics feed, reaction efficiencies were measured and conversion and selectivities are shown in Table 2.

To demonstrate the invention, the positions of the two reactors were reversed and the trichloroethylene was fed to the product stream between the reactors. The conversions and selectivities are shown in Table 2.

TABLE 2

| Reactor No. 1 | Reactor No. 2 | Trichloroethylene Conversion (%) | % Yields from trichloroethylene | | | R134a Selectivity (%) | R134a + R133a Selectivity (%) | CHCl:CF$_2$ Level in organic product (ppm) |
|---|---|---|---|---|---|---|---|---|
| | | | R133a | R134a | By-Products | | | |
| Comparison (One reactor only) | | | | | | | | |
| 250° C. | — | 97.6 | 90.5 | 0.4 | 6.7 | 0.4 | 93.2 | 31 |
| Comparison (Series) Reactors | | | | | | | | |
| 250° | 360° C. | 96.2 | 41.9 | 42.4 | 11.9 | 44.1 | 87.6 | 979 |
| Invention (Reverse Series Reactors) | | | | | | | | |
| 360° C. | 250° C. | 98.2 | 2.5 | 87.5 | 8.2 | 89.1 | 91.7 | 29 |

What is claimed is:

1. A method for the manufacture of 1,1,1,2-tetrafluoroethane which comprises the steps of:

(A) contacting a mixture of 1,1,1,-trifluoro-2-chloroethane and hydrogen fluoride with a fluorination catalyst at a temperature in the range of about 280° to 450° C. in a first reaction zone to form a product containing 1,1,1,2-tetrafluoroethane and hydrogen chloride together with unreacted starting materials, (B) passing the total product of step (A) together with trichloroethylene to a second reaction zone containing a fluorination catalyst at a temperature in the range of about 200°–400° C. but lower than the temperature, in step (A) to form a product containing, 1,1,12-tetrafluoroethane 1,1,1,-trifluror-2-chloroethane, hydrogen chloride and unreacted trichloroethylene, (C) treating the product of step (B) to separate 1,1,1,2-tetrafluoroethane and hydrogen chloride from 1,1,1-trifluoro-2-chloroethane, unreacted hydrogen fluoride and trichloroethylene, (D) feeding the 1,1,1-trifluoro-2-chloroethane mixture obtained from step (C) together with hydrogen fluoride to said first reaction zone (step (A)), and (E) recovering 1,1,1,2-tetrafluoroethane from the 1,1,1,2-tetrafluoroethane and hydrogen chloride separated out in step (C).

2. A method as claimed in claim 1 wherein 2 to 6 moles of hydrogen fluoride per mole of 1,1,1-trifluoro-2-chloroethane are fed into the first reaction zone in step (A).

3. A method as claimed in claim 1 or claim 2 wherein the temperature in the first reaction zone in step (A) is in the range of from 305° C. to 385° C.

4. A method as claimed in claim 1, 2 or 3 wherein 15 to 60 moles of hydrogen fluoride per mole of trichloroethylene are fed into the second reaction zone in step (B).

5. A method as claimed in claim 1 wherein the temperature in the second reaction zone in step B is in the range of from 220° C. to 350° C.

6. A method as claimed claim 1 wherein the contact time in step (A) and in step (B) is from 5 seconds to 30 seconds.

7. A method as claimed in claim 1 wherein the reactions in step (A) and step (B) are carried out at a pressure of from 5 bars to 20 bars.

8. A method as claimed in claim 1 which is operated continuously.

9. A method as claimed in claim 1 wherein said first and second reaction zones are provided by adiabatic reactors.

10. A method as claimed in claim 1 wherein the trichloroethylene fed into the second reaction zone in step (B) together with the product stream from step (A) is added to said product stream from step (A) in order to heat the trichloro-ethylene and cool the product stream in advance of the second reaction zone.

* * * * *